# United States Patent [19]

Robins et al.

[11] 4,093,617
[45] June 6, 1978

[54] 3,5,7-TRISUBSTITUTED PYRAZOLO[1,5-a]PYRIMIDINES

[75] Inventors: Roland K. Robins, Santa Ana; Darrell E. O'Brien, Mission Viejo; Thomas Novinson, Costa Mesa, all of Calif.

[73] Assignee: ICN Pharmaceuticals, Inc., Irvine, Calif.

[21] Appl. No.: 653,013

[22] Filed: Jan. 28, 1976

Related U.S. Application Data

[63] Continuation of Ser. No. 520,731, Nov. 12, 1974, abandoned, which is a continuation of Ser. No. 273,465, Jul. 20, 1972, abandoned, which is a continuation-in-part of Ser. No. 206,538, Dec. 9, 1971, abandoned.

[51] Int. Cl.² .................. C07D 487/04; A61K 31/415
[52] U.S. Cl. ...................................... 544/281; 424/251
[58] Field of Search .................................. 260/256.4 F

[56] References Cited

U.S. PATENT DOCUMENTS 3,920,652  11/1975  Springer et al. ............. 260/256.4 F
3,925,385  12/1975  O'Brien et al. ............... 260/256.4 F

FOREIGN PATENT DOCUMENTS 2,257,547  6/1973  Germany.

OTHER PUBLICATIONS

"Chemical Abstracts", vol. 62, 1965, col. 14609h.
"Chemical Abstracts", vol. 64, 1966, col. 2102f.
"Chemical Abstracts", vol. 58, 1963, col. 13949c.
"Chemical Abstracts", vol. 76, 1972, col. 85779c.
Reimlinger, et al., Chem. Ber., vol. 103, 1970, pp. 3252–3254.
Yale, J. Med. and Pharm. Chem., vol. 1, No. 2, (1959), pp. 121–133.

*Primary Examiner*—Donald G. Daus
*Assistant Examiner*—James H. Turnipseed
*Attorney, Agent, or Firm*—K. H. Boswell

[57] ABSTRACT

3,5,7-Trisubstituted pyrazolo[1,5-a]pyrimidines are disclosed of the general formula

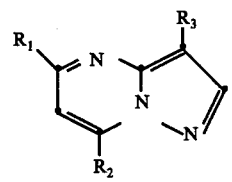

wherein $R_1$ is $CF_3$ or $C_1$–$C_9$ alkyl; $R_2$ is $CF_3$ or $C_1$–$C_9$ alkyl; and $R_3$ is halogen. Such compounds are useful as inhibitors of 3',5'-cyclic AMP phosphodiesterase enzyme.

8 Claims, No Drawings

3,5,7-TRISUBSTITUTED PYRAZOLO[1,5-a]PYRIMIDINES

This application is a continuation-in-part of Ser. No. 520,731 filed Nov. 12, 1974, now abandoned which was a continuation of Ser. No. 273,465 filed July 20, 1972, now abandoned, which was a continuation-in-part of Ser. No. 206,538, filed Dec. 9, 1971, now abandoned, entitled "3,5,7-Trisubstituted Pyrazolo [1,5-a]pyrimidines".

BACKGROUND OF THE INVENTION

As reported by Sutherland et al in "Cyclic AMP", *Am. Rev. Biochem.* 37, 149 (1968), cyclic adenosine monophosphate (C-AMP) has been established as an intracellular "second messenger", mediating many of the actions of a variety of different hormones. According to this theory, first messenger hormones, such as epinephrine and norepinephrine, influence adenyl cyclase contained at or within cell walls to form intracellularly cyclic AMP from adenosine triphosphate upon receipt of the extra-cellular hormone signal. The formed cyclic AMP in turn functions as a second messenger and stimulates intracellular functions particular to the target cells of the hormone. Cyclic AMP has thus been shown to "activate" protein kinases, which in turn produce physiological effects such as muscle contraction, glycogenolysis, steriodogenisis, and lipolysis.

Cyclic AMP is degraded, however, in vivo by phosphodiesterase enzymes, which catalyze hydrolysis of the cyclic purine nucleotide to 5'-adenosine monophosphate with a consequent loss of function. It has accordingly been suggested that substituted cyclic AMP analogs which are more resistant to phosphodiesterase degradation than the naturally occurring cyclic nucleotide might be administered in aid of lagging cellular processes. Synthetic production of such compounds, however, is quite costly. It would be advantageous, therefore, to enhance the beneficial effects of naturally produced cyclic AMP by administering compounds which are capable of inhibiting the undesirable effects of phosphodiesterase enzymes.

Sutherland et al, in *Circulation* 37, 279 (1968), suggest that the pharmacological effects of theophylline, which has the structure

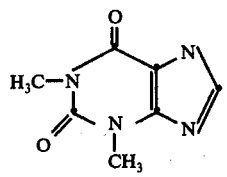

are the result of its ability to inhibit the action of phosphodiesterase enzymes. Theophylline has thus been employed in lieu of the adenyl cyclase-stimulating hormones, epinephrine and norepinephrine, as a heart stimulants following cardiac arrest and in refractory asthma cases as a bronchial dilator. Theophylline, however, does not selectively inhibit phosphodiesterase, but rather gives general stimulation to the central nevous system. Accordingly, the use of theophylline can make the recipient nervous and irritable and can also create cardiovascular effects, i.e., rapid beating. By the same token, theophylline is not as potent as a phosphodiesterase inhibitor as is desired and consequently has to be used in larger quantities, which, of course, can further the undesirable effects enumerated above.

F. L. Rose et al, in articles appearing in *J. Chem. Soc.* 5642 (1963), 3357 (1965), and 1593 (1969), reported a number of triazolo[2,3-c]-pyrimidines and triazolo[4,3-c]pyrazines (for example, compounds 1 and 2 shown below) which are structurally related to theophylline and capable of protecting animals from histamine-induced bronchospasm.

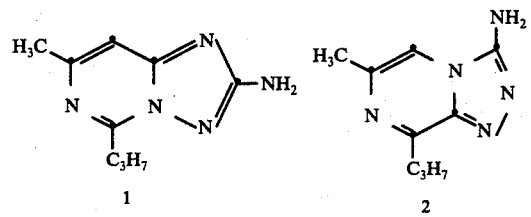

Based on the possibility that the pharmacological effects of compounds 1 and 2 may be the result of the same biochemical mechanism as proposed for theophylline, various 5,7-dialkyl-pyrazolo[1,5-a]pyrimidines were prepared and found to possess phosphodiesterase enzyme inhibitory capability, as set forth in our aforesaid application, Ser. No. 273,465. This accordingly led to the investigation of additional 3,5,7-substituted pyrazolo[1,5-a]pyrimidines.

SUMMARY OF THE INVENTION

Compounds of the following structure are provided which are capable of inhibiting the enzyme phosphodiesterase:

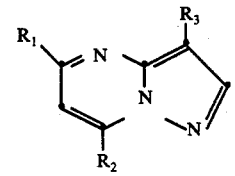

wherein $R_1$ is $CF_3$ or $C_1$–$C_9$ alkyl; $R_2$ is $CF_3$ or $C_1$–$C_9$ alkyl; and $R_3$ is halogen.

As will be seen from the following description and examples, the alkyl substituents preferably contain from 1 to 8 carbon atoms.

DETAILED DESCRIPTION OF THE INVENTION

The procedure for preparation of the 5,7-dialkyl compounds of this invention follows generally that reported by Y. Makisumi, *Chem. Pharm. Bull.* (Tokyo) 10, 612 (1962) wherein 3-aminopyrazole or 3-amino-4-carbethoxypyrazole is condensed with pentane-2,4-dione to provide 5,7-dimethylpyrazolo[1,5-a]pyrimidine or the 3-carbethoxy derivative.

It should be noted that condensation of 3-aminopyrazole with symmetrical diketones such as pentane-2,4-dione, heptane-3,5-dione and nonane-4,6-dione leads to formation of 5,7-diethyl and 5,7-dipropyl-pyrazolo[1,5-a]pyrimidines (Compound 3). Such 5,7-dialkylpyrazolo[1,5-a]-pyrimidines may be readily halogenated in the 3 position, as for example, bromination with N-bromosuccinimide.

Condensation of unsymmetrical β-diketones, however, such as hexane-2,4-dione, with 3-aminopyrazole, yields the corresponding 5-methyl7-alkyl and 7-methyl- 5-alkyl isomers (3) and (4). Because of similarity of the physical properties of the two isomers, separation is difficult and for that reason the crude isomeric mixture of (3) and (4) may be converted into higher melting derivatives, such as compounds (5), (6), and (7), which may be separated by column chromatography and fractional recrystallization techniques. Similarly, condensation of 3-amino-4-carbethoxypyrazole with hexane-2,4-dione provides a mixture of the correspondingly substituted compounds (3) and (4) which may be separated in the same manner. By the same token, condensation of 1-phenyl-1,3-butanedione with 3-aminopyrazole yields and isomeric product which may be recrystallized without chromatography to yield 7-methyl-5-phenylpyrazole[1,5-a]pyrimidine. That this isomer was obtained rather than 5-methyl-7-phenylpyrazole[1,5-a]pyrimidine was demonstrated by comparison of physical data including nmr, ultraviolet spectrum and melting point, with the 5-methyl isomer previously reported by H. Dorn et al, *J. Pr. Chem.* 313, 969 (1971).

3-bromo5,7-dimethylpyrazolo[1,5-a]pyrimidine, permitting identification of the separated products from the bromination (and subsequent chromatography) of the isomeric mixtures (3), (4) arising from the condensation of 3-aminopyrazole with unsymmetrical β-diketones.

This invention is further described and illustrated in the following examples, in which all parts and percentages are by weight and all temperatures in degrees Centigrade unless otherwise indicated. Melting points were taken on a Thomas-Hoover melting point apparatus and are uncorrected. Infra-red and nuclear magnetic resonance spectra were determined on a Perkin-Elmer 257 grating infra-red spectrophotometer and on a Hitachi Perkin-Elmer R-20A high resolution nuclear magnetic resonance spectrophotometer, respectively. Hydrogenations were carried out on a Parr hydrogenator at room temperature and at a starting pressure of 42 lbs/in$^2$ of hydrogen. All samples displayed a single spot on thin layer chromatography and were analyzed by the heterocyclic Chemical Corporation of Harrisonville,

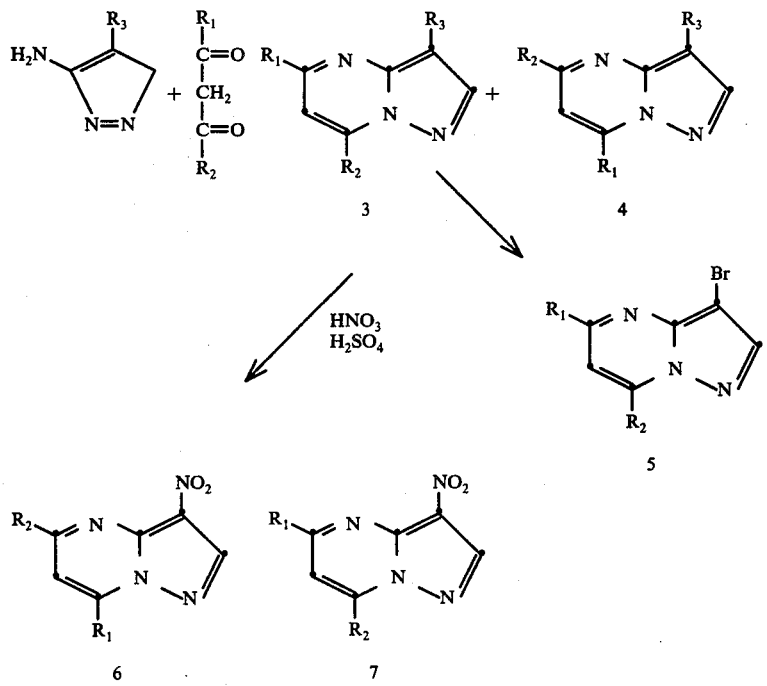

Structural proof to distinguish between 5-methyl-7-alkyl (4) and 5-alkyl-7-methyl (3) isomers is based on the nmr assignment of the well separated C$_5$- and C$_7$-methyl signals. It has been demonstrated [H. Reimlinger, Chem. Ber., 103, 1900, 3252 (1970), 104, 2232, 2237 (1971)] in 5,7-dimethylpyrazolo[1,5-a]pyrimidine that the C$_7$-methyl signal, being adjacent to the bridgehead nitrogen, is deshielded to a greater extent than the C$_5$-methyl signal (adjacent to the pyrimidine N$_4$ nitrogen) and thus occurs at a lower field. The assignments are 2.56δ for C$_5$-CH$_3$ and 2.73δ for C$_7$-CH$_3$ in deuterochloroform. Since the replacement of a longer alkyl chain (ethyl, propyl, etc.) for one methyl group at either C$_5$ or C$_7$ would not be expected to change the chemical shift of the remaining methyl group, the 5-methyl-7-alkyl isomer can be distinguished from the 7-methyl5-alkyl isomer via nmr (in deuterochloroform) and the percent of each isomer in the isomeric mixture can be estimated from the integration of the signals. Similarly, the C$_5$-methyl signal occurs at 6.60δ and the C$_7$-methyl signal at 2.72δ (in deuterochloroform) for the nmr of Missouri. Where analyses are indicated only by symbols of the elements or functions, analytical results obtained for those elements or functions were within ± 0.4% of the theoretical values.

EXAMPLE I

3-Bromo-5,7-dimethyl pyrazolo[1,5-a]pyrimidine

To a solution of 2.0g (13.6 mmloes) 5,7-dimethyl pyrazolo[1,5-a]-pyrimidine [Y. Makisumi, Chem. Pharm. Bull. (Tokyo) 10, 612 (1962)] in CHCl$_3$ (25 ml) was added N-bromosuccinimide (NBS) [2.42 g (13.6 mmloes)]. This mixture was heated on the steam bath for 10 minutes, and then allowed to cool to room temperature. The clear yellow solution was then added to an ice cold solution of potassium hydroxide (50 ml, 2N) with good stirring. The CHCl$_3$ layer was dried over Na$_2$SO$_4$, then chromatographed on basic alumina. Evaporation on the CHCl$_3$ eluant afforded a white solid which was further purified by recrystallization from petroleum ether (30°–60°) to give 1.7g (56%) of analytically pure product; mp 115°–6°.

Anal. ($C_8H_8N_3Br$) C, H, N.

NMR ($CDCl_3$) four singlets in a ratio of 3:3:1:1 at 2.60$\delta$ ($CH_3$), 2.72$\delta$ ($CH_3$), 6.62$\delta$ (H at 6 position), and 8.10$\delta$ (H at 2 position). The spectrum of the starting material exhibited peaks at 2.56$\delta$ ($CH_3$ at $C_7$), 2.73$\delta$ ($CH_3$ at $C_5$), 6.58$\delta$ ($C_6$-H), 6.60$\delta$ ($C_3$-H), and 8.11$\delta$ ($C_2$-H) (protons at $C_2$ and $C_3$ were coupled, J = 2.1cps).

EXAMPLE II

3-Chloro-5,7-dimethyl pyrazolo[1,5-a]pyrimidine

In a manner similar to the preparation of Example I, the treatment of 5,7-dimethyl pyrazolo[1,5-a]pyrimidine [1.20g (8.15 mmoles)] with N-chlorosuccinimide (NCS) [1.33g (10.0 mmoles)] afforded 963 mg (65%) of analytically pure product; mp 89°–90°.

Anal. ($C_8H_8N_3Cl$) C, H, N.

EXAMPLE III 5,7-Dimethyl 3-iodo pyrazolo[1,5-a]pyrimidine

A solution of ICl [5.0g (27 mmoles)] in $CHCl_3$ (50 ml) was added to a stirred solution of 5,7-dimethyl pyrazolo[1,5-a]pyrimidine [2.96g (20 mmoles)] in $CHCl_3$ (50 ml). Within a few minutes, the mixture became warm and crystals of the hydrochloride salt of the subject compound began to separate. The mixture was warmed on the steam bath for 2-3 minutes to complete the reaction, and then refrigerated overnight. The yellow hydrochloride salt was separated by filtration, washed with $Et_2O$, and air dried. The yellow solid, which weighed 4.4g, was dissolved in water (100 ml) and this solution was made alkaline by the addition of NaOH solution (2.5N). The alkaline solution was extracted with $CHCl_3$ 3(25 ml), and the $CHCl_3$ extracts were dried over $Na_2SO_4$. The $CHCl_3$ extract was chromatographed on basic alumina, and the $CHCl_3$ eluant evaporated to dryness. The residue was recrystallized from petroleum ether (30°–60°) to afford 2.02g (37%) of analytically pure product; mp 120°–2°.

Anal. ($C_8H_8N_3I$) C, H, N.

EXAMPLE IV 5,7-Dimethyl 3-fluoro pyrazolo[1,5-a]pyrimidine

A mixture of 5,7-dimethyl pyrazolo[1,5-a]pyrimidine [1.47g (10 mmoles)], trifluoroacetic anhydride (2.0 ml), and boron trifluoride etherate (2.0 ml) in $CH_2Cl_2$ (30 ml) was heated at reflux for 24 hours. At the end of this time the red solution was cooled and added to an ice cold solution of NaOH (30 ml, 2N). The organic layer was separated and the alkaline layer extracted with $CH_2Cl_2$ 3(20 ml). The combined $CH_2Cl_2$ extracts were washed with water 2(20 ml) and dried over $Na_2SO_4$. The $CH_2Cl_2$ extract was evaporated and the residue covered with n-petane qnd chilled. The yellow white crystalline plates were separated by filtration, and recrystallized from n-heptane to yield an analytically pure product; mp 129°–30°.

Anal. ($C_8H_8N_3F$) C, H, N, F.

NMR ($CDCl_3$) four singlets in a ratio of 3:3:1:1 at 2.55$\delta$ ($CH_3$), 2.60$\delta$ ($CH_3$), 6.60$\delta$ (H at 6 position), and 8.60$\delta$ (H at 2 position).

EXAMPLE V 5,7-Dimethyl-3-nitro pyrazolo[1,5-a]pyrimidine 5,7-Dimethyl pyrazolo[1,5-a]pyrimidine [1.0g (6.8 mmoles)] was dissolved in $H_2SO_4$ (10 ml) keeping the temperature below 5°. Fuming $HNO_3$ [4 ml; sp. gr. 1.5] was added dropwise to the cold $H_2SO_4$ solution, with good stirring. The temperature during this addition was maintained below 10°. After the addition was complete, the solution was stirred at room temperature for 45 minutes and then added to 100 g of ice. The precipitated product was separated by filtration, washed well with $H_2O$, and dried. Recrystallization from $CH_3OH$ afforded 0.75 g (57%) of analytically pure product; mp 156°–7°.

Anal. ($C_8H_8N_4O_2$) C, H, N.

NMR ($CDCl_3$) singlets in a ratio of 3:3:1:1 at 2.80$\delta$ ($CH_3$), 2.85$\delta$ ($CH_3$), 7.04$\delta$ (H at 6 position), and 8.76$\delta$ (H at 2 position).

EXAMPLE VI 5,7-Dialkylpyrazolo[1,5-a]pyrimidines; General Method

The dialkyl- compounds were prepared by refluxing 0.01 mole of the appropriate alkyl dione in 20–30 ml absolute ethanol containing 1–2 drops of piperidine. After a reflux of 2–6 hours, the alcoholic solution was evaporated at reduced pressure to give an oil which was then chromatographed on basic alumina with either benzene or chloroform (procedure also removes piperidine and any excess unreacted starting materials). The products obtained as oils may be further purified by distillation in vacuo.

EXAMPLE VII

7-Alkyl-5-methyl(or aryl)pyrazolo[1,5-a]pyrimidines; General Method

These compounds were prepared in an analogous manner to the 5,7-dialkylpyrazolo[1,5-a]pyrimidines, separating mixed isomers by nitration or bromination procedures. One isomeric mixture, the 7-methyl-5-phenyl derivative, could be separated from the other isomer by chromatography on basic alumina with chloroform, without resorting to bromination or nitration of the parent ring system.

EXAMPLE VIII

5-Methyl(ethyl)-7-ethyl(methyl)pyrazolo[1,5-a]pyrimidine

The compound was prepared, as described above, from 3-aminopyrazole (8.3 g) and hexane-2,4-dione (11.4 g) in ethanol with a catalytic amount of piperidine. The product was isolated as a colorless oil (14.0 g, 87% yield) via chromatography on basic alumina with benzene. Oil, b.p. 173°–177°/0.1mm. Mass spectrum $M^+$ = 161.

Anal. Calcd. for $C_9H_{11}N_3$(MW 161): C, 67.08; H, 6.83; N, 26.08. Found: C, 66.88; H, 6.94; N, 26.22.

NMR ($CDCl_3$) indicated two isomers, 5-ethyl-7-methyl and 5-methyl-7-ethyl, with the dominant (65.35) being the latter isomer: m, 1.4$\delta$ (two triplets from the 5-ethyl and the 7-ethyl), m, 3.1$\delta$ (two quartets from the 5-ethyl and the 7-ethyl), s, 2.56$\delta$ ($C_5$-$CH_3$) and s, 2.73$\delta$ ($C_7$-$CH_3$), s, 6.58$\delta$ ($C_6$-H) and coupled s, 6.60$\delta$ ($C_3$-H) with coupled s, 8.11$\delta$ ($C_2$-H) and $J_{2,3}$=2.5 cps.

EXAMPLE IX

5-Methyl(n-propyl)-7-n-propyl(methyl)pyrazolo[1,5-a]pyrimidine

This compound was prepared from heptane-2,4-dione (8.2 g, 0.064 mole) and the dominant isomer was found to be the 5-methyl-7-n-propyl.

Yield: 15 g mixed isomers (86%) colorless semisolid, mp 40°–45°, b.p. 165°–169°/0.1 mm. Mass spectrum $M^+ = 175$.

Anal. Calcd. for $C_{10}H_{13}N_3$(MW 175): C, 68.54; H, 7.48; N, 23.98. Found: C, 68.31; H, 7.56; N, 23.79.

NMR (CDCl$_3$) m, 1.2$\delta$ ($C_5$, $C_7$-propyl); m, 1.8$\delta$ ($C_5$, $C_7$-propyl); m, 3.0$\delta$ ($C_5$, $C_7$-propyl); s, 2.58$\delta$ ($C_5$–CH$_3$) and s, 2.72$\delta$ ($C_7$–CH$_3$); s, 6.58$\delta$ ($C_6$-H) and coupled s, 6.63$\delta$ ($C_3$-H) with coupled s, 8.10$\delta$ ($C_2$-H) $J_{2,3} = 2.5$ cps.

EXAMPLE X

5,7-Diethylpyrazolo[1,5-a]pyrimidine

This compound was prepared from 6.5 g (0.05 mol) of heptane-3,5-dione and the yield of chromatographed material (white needles, mp 43°–44° C from petroleum ether) was 6.3 g (72%).

Anal. Calcd. for $C_{10}H_{13}N_3$(MW 175): C, 68.54; H, 7.48; N, 23.98. Found: C, 68.52; H, 7.58; N, 24.25.

NMR (CDCl$_3$) m, 1.4$\delta$ (both $C_5$-ethyl and $C_7$-ethyl triplets); m, 3.1$\delta$ (both $C_5$-ethyl and $C_7$-ethyl quartets); s, 6.58$\delta$ ($C_6$-H); s, 6.6$\delta$ ($C_3$-H); and s, 8.1$\delta$ ($C_2$-H), the latter two protons being coupled with $J_{2,3} = 2.5$ cps.

EXAMPLE XI

5-Methyl-7-phenylpyrazolo[1,5-a]pyrimidine

This compound was prepared from 1-phenylbutane-1,3-dione (8.1 g, 0.05 mol) in the usual manner, to give a crude product which was chromatographed on basic alumina with ether-chloroform (9:2) yielding white plates, 1.3 g (12.7%), mp 70°–71° after recrystallization from petroleum ether. This product was demonstrated to be the pure 5-methyl-7-phenyl isomer by nmr.

Anal. Calcd. for $C_{13}H_{11}N_3$(MW 209.3): C, 74.62; H, 5.30; N, 20.08. Found: C, 74.77; H, 5.20; N, 20.21.

NMR (CDCl$_3$): s, 2.82$\delta$ ($C_5$–CH$_3$); couples s, 6.71$\delta$ ($C_3$-H); s, 7.10$\delta$ ($C_6$-H) m, 7.80$\delta$ and 8.15$\delta$ ($C_7$-phenyl ABX pattern) and coupled s, 8.03$\delta$ ($C_2$-H). $J_{2,3} = 2.1$ cps.

EXAMPLE XII

5,7-Di-n-propylpyrazolo[1,5-a]pyrimidine

This compound was synthesized from nonane-4,6-dione (15.6 g, 0.10 mole) to give 17.0 g (84%) of a pale yellow oil, after chromatography.

Anal. Calcd. for $C_{12}H_{17}N_3$(MW 203): C, 70.93; H, 8.37; N, 20.68. Found: C. 71.16; H, 8.25; N, 20.85. b.p. 155°–158°/0.1 mm.

EXAMPLE XIII

3-Bromo-5,7-dialkylpyrazolo[1,5-a]pyrimidines

GENERAL METHOD

The 3-bromo compounds were each prepared by dissolving the parent dialkyl compound (0.1 mole) in chloroform (100 ml) and adding to this solution, solid N-bromosuccinimide (18 g, 0.11 mole). The mixture was then heated on a steam bath until all the solids were dissolved, then the solution was boiled for 5–10 minutes additionally. The dark red or amber solution was then poured over ice (50 g) and cold 10% sodium hydroxide solution (100 ml) was added and the two phase system was placed in an ice box (+6° C) overnight or about 20 hours. The chloroform solution was separated and washed with cold 10% sodium hydroxide (100 ml), then water (two portions of 100 ml each), and the organic solvent was dried (Na$_2$SO$_4$) and concentrated by evaporation to 50 ml, then filtered through 100 g of Woelm basic alumina and eluted with chloroform, following the chromatography via tlc on alumina plates. Evaporation of the chromatographed fractions gave white crystals of the bromo compounds (which could then be separated into 5-methyl-7-alkyl and 5-alkyl-7-methyl isomers by fractional recrystallization from benzene-petroleum ether (1:1).

EXAMPLE XIV

3-Bromo-7-ethyl-5-methylpyrazolo[1,5-a]pyrimidine

This compound was prepared from 2.6 g (0.063 mole) of the isomeric mixture of dialkyl compound to yield 2.5 g (64%) of the pure 7-ethyl-5-methyl isomer, mp 78°–79° C.

Anal. Calcd. for $C_9H_{10}N_3$Br (MW 240): C, 45.00; H, 4.16; N, 17.50. Found: C, 44.79; H, 4.38; N, 17.40.

NMR (CDCl$_3$): t, 1.43$\delta$ (ethyl); s, 2.6$\delta$ ($C_5$–CH$_3$); q, 3.10$\delta$ (ethyl); s, 6.63$\delta$ ($C_6$-H); s, 8.10$\delta$ ($C_2$-H).

The establishment of the isomer which was isolated is based on the nmr data of 3-bromo-5,7-dimethylpyrazolo[1,5-a]pyrimidine, which consists of methyl peaks at 2.60$\delta$ and at 2.72$\delta$. The peak at 2.60$\delta$ is attributed to the $C_5$–CH$_3$, i.e., the methyl group closest to the $N_4$-nitrogen not involved in the bridgehead. The peak at 2.72$\delta$ is attributed to the $C_7$–CH$_3$, i.e., the methyl group closest to the bridgehead nitrogen by virtue of its greater deshielding effect, which is in accord with similar studies by other authors [Y. Makisumi, et al, Chem. Pharm. Bull., 12, 204 (1964)].

EXAMPLE XV

3-Bromo-5-methyl-7-n-propylpyrazolo[1,5-a]pyrimidine

This compound was prepared from 1.75 g (0.01 mole) of the 5,7-dialkyl compound (mixed isomers), which was purified by chromatography on basic alumina with chloroform. A colorless oil was obtained and this soon solidified to white crystals, which upon recrystallization from benzene-petroleum ether (1:25) gave white needles, mp 88°–89° C, 1.20 g (48%).

Anal. Calcd. for $C_{10}H_{12}N_3$Br (MW 254): C, 47.24; H, 4.72; N, 16.53. Found: C, 47.30; H, 4.81; N, 16.60.

NMR (CDCl$_3$) t, 1.05$\delta$ (propyl); m, 1.8$\delta$ (propyl); s, 2.64$\delta$ ($C_5$–CH$_3$); t, 3.10$\delta$ (propyl); s, 6.59$\delta$ ($C_6$-H); s, 8.05$\delta$ ($C_2$-H).

EXAMPLE XVI

3-Bromo-5,7-diethylpyrazolo[1,5-a]pyrimidine

This compound was prepared by bromination of 1.75 g (0.01 mole) of the dialkyl compound. Chromatography on basic alumina with chloroform have 2.0 g (79%) of white needles, mp 64°–65° C.

Anal. Calcd. for $C_{10}H_{12}N_3$Br (MW 254): C, 47.24; H, 4.72; N, 16.53. Found: C, 47.10; H, 4.63; N, 16.71.

NMR (CDCl$_3$) t, 1.35$\delta$ and t, 1.43$\delta$ (from $C_5$- and $C_7$-ethyl); q, 2.98$\delta$ and q, 3.10$\delta$ from $C_5$- and $C_7$-ethyl); s, 6.63$\delta$ ($C_6$-H) and s, 8.08$\delta$ ($C_2$-H) integration 3:3:2:2:1:1. No coupling was observed for singlets at 6.63$\delta$ and 8.08$\delta$.

EXAMPLE XVII

3-Bromo-5,7-di-n-propylpyrazolo[1,5-a]pyrimidine

This compound was prepared by brominating 4.06 g (0.02 mole) of the 5,7-di-n-propyl parent compound to yield 3.5 g (62%) of white needles, mp 66°–67° C after chromatography on basic alumina (chloroform) and recrystallization from petroleum ether.

Anal. Calcd. for $C_{12}H_{16}N_3Br$ (MW 282): C, 51.06; H, 5.67; N, 14.89. Found: C, 50.85; H, 5.92; N, 15.11.

NMR ($CDC_3$) propyl groups appear as overlapping multiplets at 1.2δ, 1.8δ, and 3.0δ; s, 6.60δ ($C_6$-H); s, 8.08δ ($C_2$-H). Integration 6:4:4:1:1.

EXAMPLE XVIII

5-Methyl-7-n-nonylpyrazolo[1,5-a]pyrimidine

A mixture of 1.8 g (84 mmol) of nonylacetone [prepared according to the method of J. J. Bloomfield, *J. Org. Chem.*, 27, 2742 (1962)] 0.7 gm (84 mmol) of 3-aminopyrazole, 3 drops of piperidine and 30 ml EtOH was refluxed for 6–8 hours. The solution was evaporated and distilled to yield 0.6 gm (33%) of a pale yellow, viscous oil, b.p. 60°–65°/0.5 mm.

NMR ($CHCl_3$): m, 0.98–2.0 (14): s, 2.55 (3): s, 2.72 (3): m, 3.1 (2), d, 6.55 (1): d, 8.05 (1): $J_{2,3}$ = 2.5 Hz.

UV (MeOH) λmax = 230 mμ ($\epsilon_{max}$ 1.3 × 10⁴).

IR (neat) intense bands at 2840, 2915 $cm^{-1}$

Anal. ($C_{16}H_{25}N_3$) MW 259.39: C, 74.08; H, 9.71; N, 16.19. Found: C, 73.85; H, 9.62; N, 16.31.

EXAMPLE XIX

5,7-Bis(trifluoromethyl)pyrazolo[1,5-a]pyrimidine

A mixture of 3.45 g (41.6 mmol) of 3-aminopyrazole and 5.0 g (41.6 mmol) of 1, 1, 1, 5, 5, 5-hexafluoroacetylacetone in 30 ml EtOH containing 2 drops of piperidine, was refluxed for 8–10 hours. The mixture was cooled and evaporated in vacuo to yield an oil. The oil was extracted with hot ligroine and cooled to yield 4.2 g (75%) of the product as a yellow-white powder, mp 105°–106°.

Anal. ($C_8H_3N_3F_6$) MW 255 ¹⁹F NMR ($CDCl_3$) C, 37.64; H, 1.17; N, 16.47 $C_5$–$CF_3$ at 13 ppm Found: C, 37,80; H, 1.23; N, 16.55 $C_7$–$CF_3$ at 16.5 ppm relative to 100% TFAA at 5.4673 KHz

EXAMPLE XX

7-Isobutyl-5-methylpyrazolo]1,5-a]pyrimidine

A mixture of 4.2 g (0.05 mol) of 3-aminopyrazole and 7.1 g (0.05 mol) of 6-methyl-2,4-heptanedione in 20 ml EtOH, was refluxed, with a catalytic amount of piperidine (2–3 drops) for 35 hours. The EtOH was evaporated and the residue was extracted with hot petroleum ether, cooled and evaporated again, to yield an oil. The oil was distilled to yield 7.5 g (82%) of an amber oil, b.p. 75–77°/0.1 mm.

NMR ($CDCl_3$): d, 0.95 (6); s, 2.6 (2); s, 2.78 (3); m, 2.3 (1); d, 6.58 (1); and d, 8.1 (1).

Anal. ($C_{11}H_{15}N_3$) MW 289: C, 69.84; H, 7.93; N, 22.22. Found: C, 70.03; H, 8.05; H, 22.10.

EXAMPLE XXI

3-Bromo-7-isobutyl-5-methylpyrazolo[1,5-a]pyrimidine

A solution of 7.5 g (0.026 mol) of 7-isobutyl-5-methyl-pyrazolo-[1,5-a]pyrimidine in 60 ml chloroform was treated with 4.6 gm (0.026 mol) of N-bromosuccinimide. The mixture was stirred at ambient temperature and then allowed to cool overnight in the refrigerator. The mixture was then poured over ice (100 gm), rendered alkaline with 6N NaOH, and extracted with chloroform. The chloroform solution was separated, dried ($Na_2SO_4$), and distilled to yield 5.5 gm, (47%) of a light yellow, viscous oil, b.p. 127°–129°/1.5 mm.

Anal. ($C_{11}H_{14}N_3Br$) MW 268: C, 48.25; H, 5.22; N, 15.67. Found: C, 49.40; H, 5.40; N, 15.81.

EXAMPLE XXII

7-Isopentyl-5-trifluoromethylpyrazolo[1,5-a]pyrimidine

A solution of 2.0 gm of 3-aminopyrazole (0.024 mol) in 50 ml EtOH was refluxed with 5.0 gm of 1,1,1,-trifluoro-7-methyl-2,4-octanedione (0.024 mol) for 2 hours. The mixture was evaporated and distilled to yield 1.6 gm (48%) of a slightly yellowish oil, b.p. 103°–105°/0.5 mm.

Anal. ($C_{12}H_{14}N_3F_3$, MW 257.25) C, 56.02; H, 5.48; N, 16.23. Found: C, 56.13; H, 5.50; N, 16.48.

EXAMPLE XXIII

3-Bromo-7-isopentyl-5-(1,1,1-trifluoromethyl)-pyrazolo[1,5-a]pyrimidine

A solution of 4.0 gm (0.0155 mol) of 7-isopentyl-5-trifluoromethylpyrazolo[1,5-a]pyrimidine in 50 ml chloroform was cooled to 15° and 2.73 gm. (0.0155 mol) of N-bromosuccinimide was added. The solution was stirred for 30 minutes at ambient temperature, then poured on ice (50 gm, crushed). The chloroform layer was washed with sat. $K_2CO_3$ solution and then dried ($Na_2SO_4$) and chromatographed on neutral alumina (Woelm, grade I). Elution of the compound with chloroform, followed by evaporation of the solvent and distillation, afforded 4.0 gm (58%) of the product as an amber oil, b.p. 123°–126°/0.5 mm.

Anal. ($C_{12}H_{13}N_3F_3Br$, MW 336.3) C, 42.85; H, 3.86; N, 12.50. Found: C, 43.00; H, 4.02; N, 12.71.

EXAMPLE XXIV

5,7-Di-n-butylpyrazolo[1,5-a]pyrimidine

A mixture of 4.1 g (0.05 mol) of 3-aminopyrazole and 9.2 gm (0.05 mol) of undecan-5,7-dione [prepared by the method of J. J. Bloomfield J. Org. Chem., 27, 2742 (1962)] yield 18.5 gm, b.p. 60°–63°/1mm calc'd for $C_{10}H_{20}O_2$: C, 71.73; H, 10.86, Found C, 71.83; H, 10.92]in 100 ml EtOH containing 2–3 drops of piperidine, was refluxed for 6 hours. The mixture was evaporated and distilled to yield 9.5 g (82.3%) of the product as a water white liquid, b.p. 110–112°/1 mm.

NMR ($CHCl_3$): t, 0.9 (3); t, 1.1 (3); m, 1.65 (8); t, 2.8 (2); t, 3.2 (2); s, 6.55 (1); d, 6.58 (1); d, 8.05 (1).

Anal. ($C_{14}H_{21}N_3$) MW 231: C, 72.72; H, 9.09; N, 18,18. Found: C, 72.86; H, 9.21; N, 18.14.

EXAMPLE XXV

3-Bromo-5,7-di-n-butylpyrazolo[1,5-a]pyrimidine

A solution of 7.0 g (0.03 mol) of 5,7-di-n-butyl-pyrazolo[1,5-a]-pyrimidine in 75 ml chloroform was treated with 5.8 g (0.035 mol) of N-bromosuccinimide at room temperature. The mixture was stirred for 5-10 minutes, then poured into ice water, made alkaline with 6N NaOH, and the organic layer separated and dried ($Na_2SO_4$). The chloroform solution was chromatographed on neutral alumina (Woelm, grade I) with chloroform as the eluant. Evaporation of the solvent and recrystallization from ligroine gave 7.15 g (72%) of the product, mp 47°–48° C.

NMR (CDCl$_3$): m, 1.0 (6) (8); m, 3.0 (6); s, 6.68 (1); s, 8.04 (1).

Anal. (C$_{14}$H$_{20}$N$_3$Br) MW 310.33: C, 54.18; H, 6.49; N, 13.53. Found: C, 54.39; H, 6.52; N, 13.14.

EXAMPLE XXVI

The compounds of the invention were tested for inhibition of phosphpodiesterase by the following procedure.

3′,5′-Cyclic-AMP phosphodiesterase (PDE) was isolated and purified from three different tissues in the following manner. Homogenates of rabbit kidney, rabbit lung, and beef heart are made in sucrose-Tris-magnesium buffer and are subjected to centrifugation at low speed to remove nuclei and cell debris. The supernatants are then centrifuged at 105,000 X g for 30 minutes, and the 105,000 X g supernatants are then fractionated using (NH$_4$)$_2$SO$_4$. The precipitation which forms at 0–30% saturation is collected by centrifugation at 20,000 X g, dissolved in Tris-magnesium buffer, and dialyzed overnight against the same buffer. A second (NH$_4$)$_2$SO$_4$ fraction is obtained by raising the concentration of the first supernatant to 50%. These two (NH$_4$)$_2$SO$_4$ fractions as well as the supernatant from the 30–50% cut were then assayed for PDE activity using the method of Appleman, Biochem. 10, 311 (1971). The first fraction obtained from both kidney and lung tissue contains a PDE with low affinity for 3′,5′-c-AMP (high Km). The second fraction exhibits a biphasic curve when the Lineweaver-Burk method of analysis is used. This indicates either the presence of two separate enzymes, one having a high and the other a low affinity for c-AMP, or one protein with two separate sites. Appleman, supra, indicates that extracts of brain yield two separate enzymes (a high Km and a low Km) which can be separated by sepharose gel chromatography.

The inhibitory studies reported in Tables I and II were performed with the low affinity (Fraction I, high Km) enzyme obtained from rabbit kidney or rabbit lung. The studies reported in Tables III and IV were performed with the high affinity (Fraction II, low Km) enzyme obtained from rabbit lung and beef heart. I$_{50}$ values were calculated in some instances from a plot of log I vs. percent I in experiments in which inhibitor concentration is varied over a wide range, at a constant 3′,5′-cyclic-AMP concentration of approximately 5 × 10$^{-4}$ M (Tables I and II) or 1.6 × 10$^{-7}$ M (Tables III and IV). The relative inhibitory activity of each compond as compared with theophylline is expressed as an α value. This value is obtained by dividing the I$_{50}$ value obtained for the particular compound being evaluated.

In most instances values were calculated from an inhibition study performed with a single concentration of test compound as long as the inhibition produced by that concentration was from 20–80%. In this instance an α value was calculated by dividing the $$\frac{\text{concentration of theophylline giving } X \text{ \% inhibition}}{\text{concentration of test substance giving the same } (X \text{ \%}) \text{ inhibition}}$$

The validity of this method has been checked by comparing α values obtained by (1) measurements at a single concentration of inhibitor and (2) measurements at four concentrations of inhibitor (I$_{50}$ determinations). α values compared in this way have been found to agree to within 10% of each other.

The basic incubation mixture contained the following substances (amounts in μmoles): $^3$H-cAMP (specific activity ~2,180 cmp/pmole), 0.00016; Tris pH 7.5, 40: MgCl$_2$, 0.5; Enzyme (cAMPphosphodiesterase), 5–50 μg protein; and 10$^{-4}$ to 10$^{-6}$ molar concentration of the inhibitor; incubation time 10 minutes at 30° C. At the end of incubation, the mixtures are heated to 90° C for 2 minutes and 100 μg of snake venom phosphodiesterase from Crotalus atrox was added and the tubes incubated for 10 minutes at 30° C. The mixture was then cooled and 1 ml of a Dowex 1-2X, 200-400 mesh suspension, prepared by mixing 100 g of the resin in 200 G H$_2$0, was added and the mixture centrifuged. An aliquot of the supernatant was used to determine counts per minute using a liquid scintillation spectrometer. Zero time values were obtained using incubations in which the cAMP phosphodiesterase was omitted from the first incubation.

TABLE I

Inhibition of 3′,5′-Cyclic AMP
Phosphodiesterase (PDE)
Isolated from Rabbit Kidney

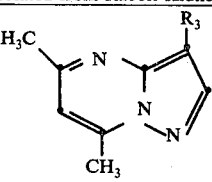

| R$_3$ | I$_{50}$[M] | I$_{50}$(theophylline)[M] | $\alpha = \dfrac{I_{50}(\text{theophylline})[M]}{I_{50}(\text{compound})[M]}$ |
|---|---|---|---|
| H* | 8 × 10$^{-4}$ | 1.6 × 10$^{-4}$ | 0.20 |
| COOC$_2$H$_5$* | 1 × 10$^{-3}$ | 2.2 × 19$^{-4}$ | 0.22 |
| COMPOUND 1* | 1.6 × 10$^{-3}$ | 2.2 × 10$^{-4}$ | 0.14 |
| Br | 1.0 × 10$^{-4}$ | 2.2 × 10$^{-4}$ | 2.20 |
| Cl | 2.4 × 10$^{-4}$ | 3.2 × 10$^{-4}$ | 1.33 |
| I | 1.3 × 10$^{-4}$ | 1.6 × 10$^{-4}$ | 1.23 |

*For comparison only

TABLE II

Inhibition of 3′,5′-Cyclic AMP Phosphodiesterase (PDE) Isolated from Rabbit Lung

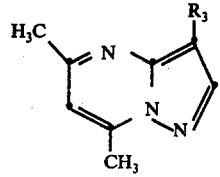

| $R_3$ | $I_{50}$[M] | $I_{50}$(Theophylline)[M] | $\alpha = \dfrac{I_{50}(\text{Theophylline}) [M]}{I_{50}(\text{Compound}) [M]}$ |
|---|---|---|---|
| H* | $2.0 \times 10^{-3}$ | $6.4 \times 10^{-4}$ | 0.32 |
| Br | $2.7 \times 10^{-4}$ | $6.4 \times 10^{-4}$ | 2.4 |
| Cl | $2.1 \times 10^{-4}$ | $6.5 \times 10^{-4}$ | 3.1 |
| I  | $2.1 \times 10^{-4}$ | $7.4 \times 10^{-4}$ | 3.5 |

*For comparison only

TABLE III

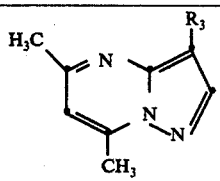

| $R_3$ | α Lung | α Heart |
|---|---|---|
| Br | 0.7 | 1.7 |
| Cl | 2.2 | 1.7 |
| I  | 3.5 | 1.5 |

TABLE IV

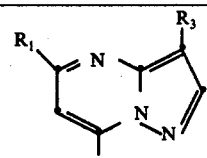

| $R_1$ | $R_2$ | $R_3$ | α Lung | α Heart |
|---|---|---|---|---|
| CH$_3$ | n-C$_3$H$_7$ | Br | 7.5 | 6.5 |
| C$_2$H$_5$ | C$_2$H$_5$ | Br | 7.4 | 6.0 |
| n-C$_3$H$_7$ | n-C$_3$H$_7$ | Br | 5.5 | 3.0 |
| CH$_3$ | C$_2$H$_5$ | Br | 7.5 | 4.0 |

In general, the phosphodiesterase inhibitors of the invention may find employment in the treatment of disorders responsive to the administration of epinephrine or norepinephrine, since in either case the result is maintenance of greater levels of c-AMP — in the first instance by retarding c-AMP degradation and in the second by stimulating its production.

Selected compounds of the invention have also demonstrated activity as antiaixety agents.

EXAMPLE XXVII

In Tables V and VI the antianxiety activity of the listed compounds is measured as a function of the compounds ability to stimulate drinking activity of the rat in a passive avoidance behavioral paradigm. For these tests male Sprague-Dawley rats weighing 175 to 200 grams were water deprived for 48 hr. and placed in environmental chambers in which water was available with a punishment contingency. Each accumulated 3 sec. of contact with the drinking tube caused a constant current source (1.2 mA DC) to be applied to the drinking tube for 2 sec. Test sessions were 5 min. in duration, commencing with delivery of the first shock. Twelve rats were treated orally 1 hr. or intraperitoneally 30 min. prior to testing. The tests are scored based on the number of shocks accepted by the treated animals at a specific dose and were compared to twelve saline control animals tested on the same day.

In Table V the activity is expressed as an ED$_{50}$. The ED$_{50}$ is the dose of the compound in mg/kg producing 50% of maximum effect and is shown for both oral (p.o.) and interperitoneal (i.p.) routes of administration.

TABLE V

Compound

| $R_1$ | $R_2$ | $R_3$ | Route | ED$_{50}$ |
|---|---|---|---|---|
| CH$_3$ | CH$_3$ | Br | i.p. | 10.5 ± 0.8 |
| " | " | " | p.o. | 9.5 ± 3.5 |
| CH$_3$ | CH$_3$ | Cl | i.p. | 2.4 ± 4.3 |
| " | " | " | p.o. | 7.8 ± 4.5 |
| CH$_3$ | CH$_3$ | I | i.p. | 10.1 ± 6.8 |
| " | " | " | p.o. | 95.9 ± 11.7 |
| CH$_3$ | CH$_3$ | F | i.p. | 40.7 ± 11.9 |
| " | " | " | p.o. | 76.2 ± 10.8 |
| CH$_3$ | CH$_3$ | H | i.p. | 20.9 ± 4.6 |
| " | " | " | p.o. | 43.6 ± 6.1 |

In Table VI the activity is expressed as the dose (i.p.) wherein the first statistically behavioral difference ($p < 0.05$ or less) from the control group occurs. Included for comparison are the commonly prescribed antianxiety drugs, chlordiazepoxide and diazepam.

TABLE VI

Compound

| $R_1$ | $R_2$ | $R_3$ | Dose mg/kg i.p. |
|---|---|---|---|
| CH$_3$ | CH$_3$ | Br | 10 |
| CH$_3$ | CH$_3$ | Cl | 10 |
| CH$_3$ | CH$_3$ | I  | 20 |
| CH$_3$ | CH$_3$ | F  | 40 |
| CH$_3$ | CH$_3$ | H  | 40 |
| Chloriazepoxide | | | 10 |
| Diazepam | | | 20 |

It is suggestive that the antianxiety activity of these compounds differs from that of other antianxiety drugs because of the differences seen in the doses necessary to potentiate the central nervous system depressant activity of both ethanol and barbiturates.

EXAMPLE XXVIII

In Table VII the results of the potentiation of the depressant effects of sodium barbital, as judged by the loss of the righting reflex in the mouse, are shown. The two most commonly prescribed antianxiety drugs, chlordiazepoxide and diazepam were used as standards. For this test male Swiss-Webster mice weighing 18 to 20 grams were housed in groups of ten and maintained on food and water ad lib. A dose of sodium barbital (100 mg/kg i.p.) was selected which did not, by itself, cause loss of righting reflex. This dose of barbital sodium (100 mg/kg) was then injected i.p. in a group of ten mice. Fifteen min. later the mice were injected i.p. with the dose of compound to be tested. The righting reflex was recorded as being present when the animal would voluntarily roll to its side when placed on its back. Mice were tested at 15 min. intervals for one hour after injection of test compound. Responses were recorded on an all-or-none basis; loss of righting reflex for 5 min. or longer was the effective criteria.

TABLE VII

Compound

| $R_1$ | $R_2$ | $R_3$ | Dose of Compound (mg/kg i.p.) which produced loss of righting reflex in 50% of treated animals |
|---|---|---|---|
| $CH_3$ | $CH_3$ | Br | 61.9 ± 12.1 |
| $CH_3$ | $CH_3$ | Cl | 60.9 ± 20.8 |
| $CH_3$ | $CH_3$ | I | 142.8 ± 10.1 |
| $CH_3$ | $CH_3$ | F | 148.5 ± 4.5 |
| $CH_3$ | $CH_3$ | H | 118.8 ± 15.7 |
| Chlordiazepoxide* | | | 6.4 ± 0.4 |
| Diazepam* | | | 0.5 ± 0.8 |

*Note: Active as antianxiety agent in the rat in about the same dose range (i.p.) as above compounds wherein $R_3$ = Br, Cl, or I.

EXAMPLE XXIX

In Table VIII the results of the potentiation of the depressant effects of ethanol, as judged by the loss of the righting reflex in the mouse, are shown. Used as a standard were the two most commonly prescribed antianxiety drugs, chlordiazepoxide and diazepam. For this test male Swiss-Webster mice weighing 18 to 20 grams were food deprived 18 hours prior to the experiment. A dose of ethanol (5 gm/kg) was selected which did not by itself cause loss of righting reflex. On each day of the experiment a group of 10 control animals received an oral injection of 25 ml/kg of a 20% v/v ethanol in water solution and were observed for loss of righting reflex. Drugs were given orally in 20 ml/kg of 1% CMC. Ethanol (5 gm/kg p.o.) was given 30 minutes after drug injection. Immediately after treatment animals were placed in individual clear plastic containers.

The righting reflex was recorded as being present when the animal would voluntarily roll to its side when placed on its back. Animals were tested for righting reflex every 15 minutes.

TABLE VIII

Compound

| $R_1$ | $R_2$ | $R_3$ | Maximum Dose of Compound (mg/kg oral) not producing loss of righting relfex in 100% of animals |
|---|---|---|---|
| $CH_3$ | $CH_3$ | Br | 400 |
| $CH_3$ | $CH_3$ | Cl | 200 |
| $CH_3$ | $CH_3$ | I | 200 |
| $CH_3$ | $CH_3$ | F | 100 |
| $CH_3$ | $CH_3$ | H | 300 |
| Chlordiazepoxide | | | 4.0 |
| Diazepam | | | 1.0 |

Some of the compounds of the invention as well as other related compounds have various other pharmacological properties as shown in our application Ser. No. 520,731 filed Nov. 12, 1974, for which this application is a continuation-in-part thereof. Also 5,7-dimethylpyrazolo-[1,5-a]pyrimidine and 3-ethoxy-5,7-dimethylpyrazolo[1,5-a]pyrimidine are noted useful as anticancer drugs in Japanese Patent 7983 (62) *Chemical Abstracts*, Vol. 59, 8764f.

We claim:

1. A compound of the structure

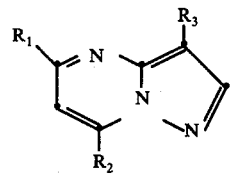

wherein $R_1$ is $C_1$-$C_3$ alkyl; $R_2$ is $C_1$-$C_3$ alkyl; and $R_3$ is halogen.

2. A compound of claim 1 wherein $R_1$ and $R_2$ are $CH_3$ and $R_3$ is halogen.

3. A compound of claim 2 wherein $R_1$ and $R_2$ are $CH_3$ and $R_3$ is iodo.

4. A compound of claim 2 wherein $R_1$ and $R_2$ are $CH_3$ and $R_3$ is floro.

5. A compound of claim 1 wherein $R_1$ and $R_2$ are ethyl and $R_3$ is halogen.

6. A compound of claim 1 wherein one of $R_1$ or $R_2$ is methyl and the other is ethyl and $R_3$ is halogen.

7. 3-Bromo-5,7-dimethylpyrazolo[1,5-a]pyrimidine.

8. 3-Chloro-5,7-dimethylprazolo[1,5-a]pyrimidine.

* * * * *